(12) United States Patent
Tsuchiya et al.

(10) Patent No.: US 8,235,934 B2
(45) Date of Patent: Aug. 7, 2012

(54) FUNCTIONAL THIN TUBE DEVICE (75) Inventors: Kazuyoshi Tsuchiya, Hiratsuka (JP);
Akifumi Morishima, Hiratsuka (JP);
Yasutomo Uetsuji, Hiratsuka (JP);
Takehiro Fukuzaki, Hiratsuka (JP)

(73) Assignee: Tokai University Educational System, Tokyo (JP)

( * ) Notice: Subject to any disclaimer, the term of this patent is extended or adjusted under 35 U.S.C. 154(b) by 153 days.

(21) Appl. No.: 12/527,765

(22) PCT Filed: Feb. 20, 2008

(86) PCT No.: PCT/JP2008/052886
§ 371 (c)(1),
(2), (4) Date: Sep. 11, 2009

(87) PCT Pub. No.: WO2008/102817
PCT Pub. Date: Aug. 28, 2008

(65) Prior Publication Data
US 2010/0094223 A1 Apr. 15, 2010

(30) Foreign Application Priority Data

Feb. 22, 2007 (JP) ................................ 2007-042992

(51) Int. Cl.
*A61B 17/20* (2006.01)
(52) U.S. Cl. .......................................... 604/22; 422/549
(58) Field of Classification Search ................. 417/211; 422/549; 604/22, 151; 606/147
See application file for complete search history.

(56) References Cited

U.S. PATENT DOCUMENTS

| 5,630,837 | A  | * | 5/1997  | Crowley ............................ 601/2 |
| 6,241,703 | B1 | * | 6/2001  | Levin et al. ...................... 604/22 |
| 6,368,299 | B1 | * | 4/2002  | Cimino ............................. 604/22 |
| 2002/0161325 | A1 | * | 10/2002 | Hansmann ........................ 604/22 |
| 2003/0065321 | A1 | * | 4/2003  | Carmel et al. ................... 606/41 |
| 2003/0141974 | A1 | * | 7/2003  | Allen ............................ 340/545.1 |
| 2004/0243182 | A1 | * | 12/2004 | Cohen et al. ....................... 607/2 |
| 2006/0064081 | A1 | * | 3/2006  | Rosinko ........................... 606/27 |
| 2007/0093745 | A1 | * | 4/2007  | Steward et al. ................. 604/22 |
| 2008/0114254 | A1 | * | 5/2008  | Matcovitch et al. ........... 600/463 |

FOREIGN PATENT DOCUMENTS

| JP | 63-057900   | 3/1988  |
| JP | 05-026170   | 2/1993  |
| JP | 2003-106262 | 4/2003  |
| JP | 2003-286958 | 10/2003 |
| JP | 2004-232077 | 8/2004  |

* cited by examiner

*Primary Examiner* — Jackie Ho
*Assistant Examiner* — Gerald Landry, II
(74) *Attorney, Agent, or Firm* — Squire Sanders (US) LLP (57) ABSTRACT

The object of the invention is to provide a functional thin tube device in which a pump and a liquid drawing device are constituted to be not separate without a sophisticated channel design and to correspond to various applications. A functional thin tube device includes a hollow tubular body, a plurality of vibrating ring bodies mounted as being kept in contact with the tubular body spaced an interval along an axial direction on an outer circumference of the tubular body, and an energy supply means of energy for vibrating the vibrating ring bodies. The energy supply means is constituted to supply energy such that the displacement caused by vibrations is mutually different among the vibrating ring bodies.

7 Claims, 11 Drawing Sheets

FIG.11A PZT element

FIG.11B PZT element with silicon tube

FUNCTIONAL THIN TUBE DEVICE

BACKGROUND

1. Field

The present invention relates to a functional thin tube device available for a case where body liquid such as blood is drawn, or where used as an analyzing needle, an injector of medical liquid, etc. in various fields such as a medical field or biological study field, or where the liquid is transported in a minute area.

2. Description of the Related Art

In general, a hollow tube as a channel path and a pump for energizing the liquid to flow in the tube are required for transportation of a small amount of liquid (movement, drawing, supply, carry, etc.) in the field of a medical care and a biological study. As the pump is an important component in the field of drawing small amounts of blood and in the field of medical equipment for the purpose of medical dosing, the important function such as the control of flow rate and volume of flow is required for the pump to transport the liquid through the hollow tube. In the field of the development of measuring devices of blood sugar level, which is, in particular, popular in the field of medical care, it is important for the pump to be able to deal with a small amount of liquid such as blood.

In a conventional blood sugar level measuring device for testing diabetes, approximately 10 ml of blood of outpatients is drawn by an injector based on the pharmaceutical affairs law, and the blood sugar level thereof is measured by a well-known blood-analysis system using a flow injection method having a centrifuge and a pump function. At present, simplification, compactization, and invasions to the human body are required. Therefore, disposal sensors for self-testing of blood sugar level have been developed to be able to measure the blood sugar level at an extremely small amount like being less than or equal to $1\mu$ liters, and are commercially available for a portable blood analysis system.

The above-mentioned disposal sensor for management of self-blood sugar level is required (1) for injection movement for piercing the injection measurement device such as a lancet in a finger or abdomen, and (2) for sophisticated manual operation for sucking the about $1\mu$ liters blood as exuded at a lancer spot by a tester himself. This can be undesirable for patients. The outside diameter of a needle for the lancet necessitates hundreds of $\mu$ meters. Then, the influence to the human body owing to the drawing blood, in particular, significant discomfort, can result. Though the micro pump for drawing blood using an extremely thin needle so as to reduce pain and discomfort has been developed and studied, in some cases devices are required to be more compact than such needles for the pump function. On the other hand, the micro machine technique (MEMS: micro electro mechanical systems) of manufacturing devices such as a micro machine device provide opportunities to develop the transportation of a small amount of liquid chemical and a drawing small amounts of blood.

For example, the following technique has been known as the above-mentioned method for manufacturing such a micro machine device. This technique includes, at first as "Lab on a chip", a small flow path on a glass plate or high polymer base plate to seal by an adhesion of an elastic body such as rubber. Further, the functional material for obtaining the force by transforming the electrical energy into the mechanical energy is placed on the elastic body. The flow function is applied to the device itself by applying forces from the top of liquid sealing rubber thereto. For example, this kind of technique has been disclosed, for example, in Japanese Patent Unexamined Laid-Open Publication No. Heisei 5-26170.

However, as the above conventional micro machine device is required for a sophisticated channel design, it is difficult to design or process the device into a shape other than a plate-like shape. As in a conventional blood sugar level measuring device, the development of both a pump and a blood (liquid) drawing device is required. Since the channel design is formed on a base plate, it has some significant limitations in how and where it can be used.

The present invention is considered in view of the present situation as above mentioned. The present invention is constituted to be simple, without requiring a sophisticated channel design by integrating a pump and a channel. Thus, an object of the present invention is to provide a functional thin tube device that can be used in various applications.

SUMMARY

The inventors have analyzed a movement of body structure of an earthworm and tried to apply it to a structure of the functional thin tube device, when they thought that the pump function was integrally constituted in a thin tube for enabling the fluid to move. That is, as an earthworm has a two-layer muscle composed of a longitudinal muscle along a longitudinal direction of the body and a ring-shaped muscle along a circumferential direction thereof. The behavior of peristaltic movement in earthworms has been known to be made by the contraction of muscles and the change of length and width of the body. When a constitution for performing the same movement as the above peristaltic movement was obtained by vibrations, the inventors considered that it would be possible to provide a micro device and to design a device having both a pump function and transportation function.

In the present invention, the inventors paid attention to the fact that the peristaltic movement, which is like a way of movement of human intestines or an earthworm, is essentially a progressive wave. In an ultrasonic wave motor, as an example of a progressive wave which is put in practice and commerce, an ellipsoidal movement occurs on any point of the surface of vibrating body by the progressive wave caused by the vibration of a piezoelectric material. Then, it has been already known that a rotating movement occurs by shifting a moving body (rotor) from the initial position due to the friction cased by the ellipsoidal movement of the vibrating body. It has also been known that a frictional force prevails against gravity or inertia in a microscopic area like an extremely thin tube as the liquid flowed, in a case where the above phenomenon is applied to the fluid.

Accordingly, the progressive wave, which occurs on a surface of an extremely thin tube by an addition of dynamic vibration transmitting from the ring-shape vibrating ring body forming a film in the extremely thin tube, transmits vibrations from an inner wall of the extremely thin tube to the liquid and the friction occurs between the liquid and the inner wall of the extremely thin tube. The present invention has been made after the verification of a mechanism to flow the liquid in the tube according to the frictional function caused by the vibration as transmitted to the liquid.

In one embodiment, a functional thin tube device relating to the present invention includes a hollow tubular body, a plurality of vibrating ring bodies in contact with the tubular body spaced an appropriate interval along an axial direction on an outer circumference of the tubular body, and an energy supply means for vibrating the vibrating ring body. The energy supply means is configured to supply energy such that amounts of displacement caused by vibrations are mutually different among the vibrating ring bodies.

The above functional thin tube device is constituted to have different amounts of displacement of the vibrating ring bodies. For example, when different vibrations caused by the vibrating ring body placed at an even position or at an odd position occur, the progressive waves are created and are different in size in the liquid inside the tubular body. Thus, this synthesis of progressive waves results in an occurrence of the progressive wave, having an ellipsoidal orbit, in the liquid inside the tubular body. The progressive wave having the ellipsoidal orbit makes the liquid in the tubular body more in a transporting direction. In addition, the functional thin tube device can be used as a means for connecting various equipment such as an injector, by arranging a tip thereof to be at a right angle.

Accordingly, the functional thin tube device can be made smaller in size, as the vibrating ring body equivalent to a pump section and a tubular body equivalent to a portion for transporting the liquid are integrally formed. Thus, the functional thin tube device is available in a microscopic portion. The functional thin tube device can control the volume of flowing or the flow rate of the liquid as transported by the displacement of the vibrating ring body and the timing of vibration.

In the above mentioned functional thin tube device, the vibrating ring body can include a piezoelectric element formed like a ring shape, and a metal electrode provided on an inner surface and on an outer surface of the piezoelectric element. Further, the energy supply means may be, for example, a voltage supply means applying the voltage to the piezoelectric element.

In such a constitution, the functional thin tube device can also provide a device having a tubular body as formed to be smaller in diameter by the spattering pile method.

In addition, the tubular body may be made of metal and formed to be an edge surface of an injector, of which the top end has a sharp angle. Accordingly, the functional thin tube device can be made to be smaller and miniaturized in size so as to reduce pain and discomfort when human skin is pierced with an injector.

The tubular body may be made of flexible material like rubber or plastics, thus to be able to extend an available area thereof.

The vibrating ring body may be configured to form a groove portion or a notch portion along an axial direction of the tubular body.

In such a functional thin tube device, the groove portion or the notch portion makes the width of vibration of the vibrating ring body to be larger in amplitude as compared with a ring-shape state. Then, the functional thin tube device can extend an area of dynamic range, in which the flow rate can be preferably controlled at the time of the transportation of liquid in the tubular body.

Further, in the functional thin tube device, the voltage supply means may be constituted to apply with a gradient of voltage in order to lower the voltage as applied toward a transportation direction of liquid transporting in the tubular body.

In such a functional thin tube device, it is easy to transport the liquid flowing in the tubular body toward the transportation direction, and also to transport the highly viscous liquid. In addition, the voltage supply means is configured to provide a gradient of voltage by directly changing the voltage, and to provide a gradient of voltage with the resistance arranged in a line between the voltage supply means and the piezoelectric element.

The energy supply means can be configured to supply energy such that the vibration of the vibrating ring body placed at an even position or at an odd position becomes a sympathetic frequency of the tubular body.

In such a configuration, the functional thin tube device can raise an efficiency of transportation of the liquid by the progressive wave having an ellipsoidal orbit to make larger vibration relative to the tubular body.

The energy supply means can be configured to supply energy such that the displacement occurring in either one of the vibrating ring body placed at an even position or at an odd position is larger.

In such a configuration, the vibrating ring body supplies the vibration to the tubular body. Then, it is easier to transport the liquid inside the tubular body by the help of the progressive wave.

DETAILED DESCRIPTION

Hereinafter, an embodiment for carrying out the present invention will be described in detail with reference to drawings.

Figure 1A:
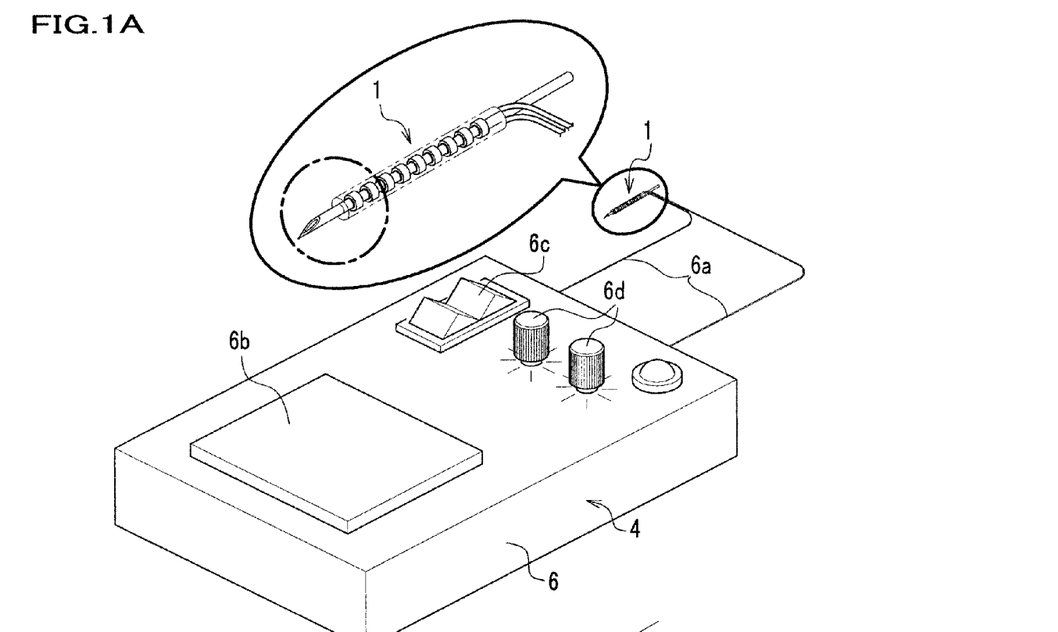
FIG. 1A is a perspective view showing a whole thin tube of a functional thin tube device according to an embodiment of the present.
Figure 1B:
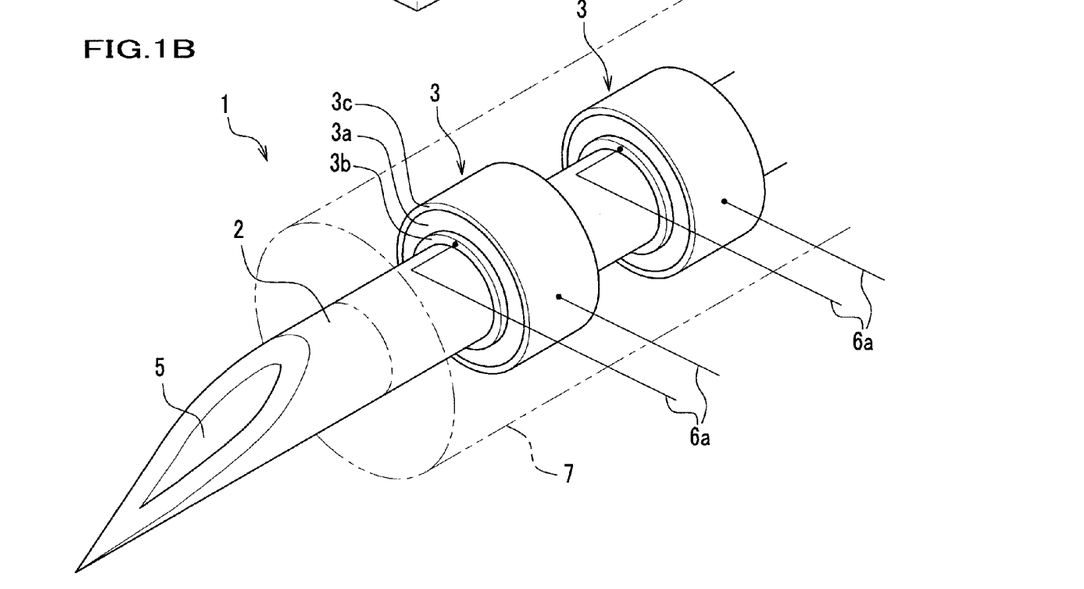
FIG. 1B is a perspective view showing an enlarged tip portion of the thin tube.
Figure 2:
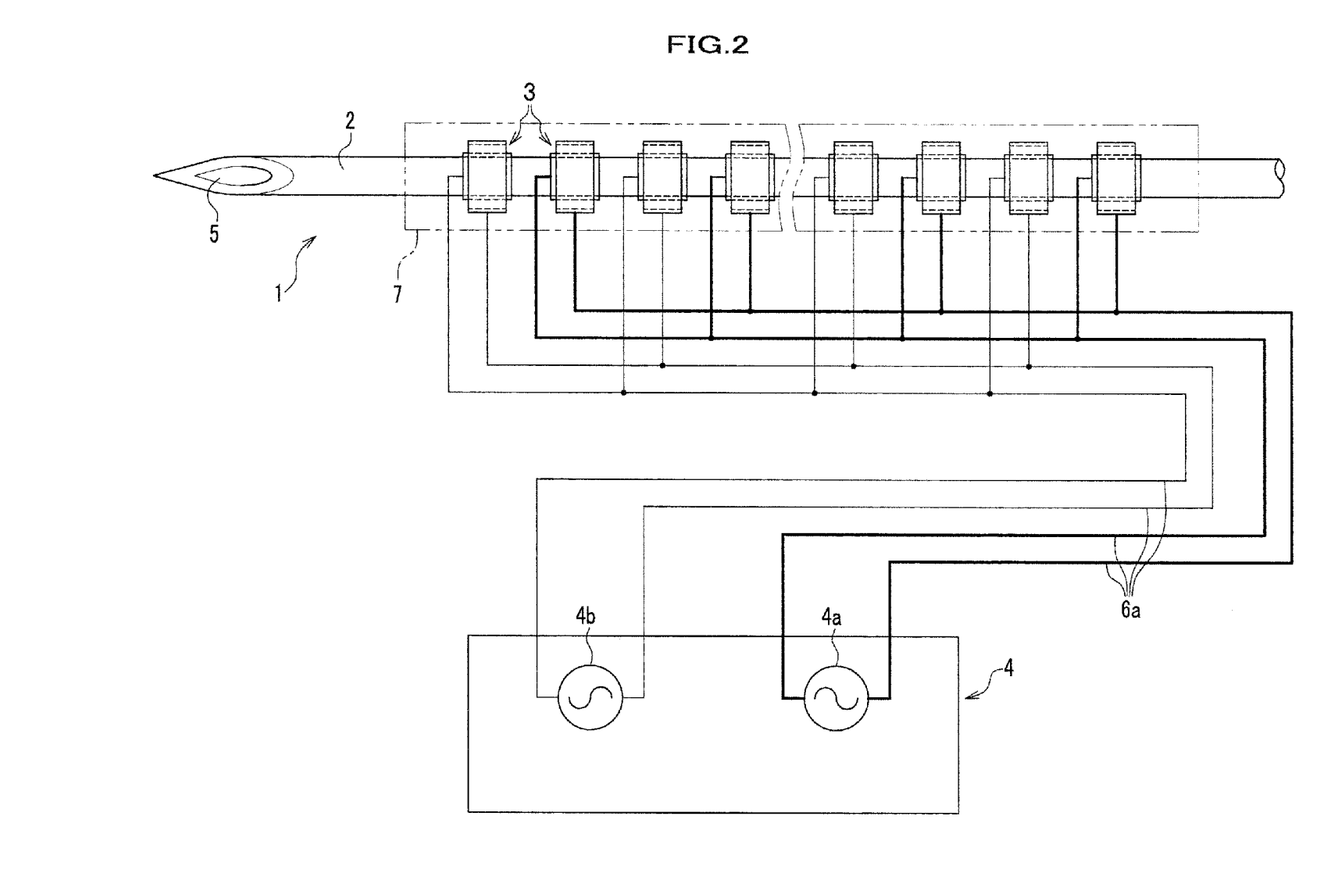
FIG. 2 is a schematic view showing the functional thin tube device according to an embodiment of the present invention.

FIG. 1A is a perspective view showing a thin tube of the functional thin tube device in an exaggerated size. FIG. 1B is a perspective view showing an enlarged tip portion of the thin tube. FIG. 2 is a schematic view of the overall functional thin tube device.

As shown in FIG. 1 and FIG. 2, the functional thin tube device 1 is provided with a tubular body 2, a thin tube composed of a plurality of vibrating ring bodies 3 as integrally formed to space an appropriate interval in an axial direction of the tubular body 2, and a voltage supply means 4 as an energy supply means applying vibrations to the vibration ring body 3 of the thin tube. The functional thin tube device 1 has an edge surface of an injector formed in one end of the tubular body 2.

The tubular body 2 can be a thin tube made of metal as one example in this embodiment. The tubular body 2 is formed by a material having an adaptable property for human body such as titanium or titanium alloy. The tubular body 2 may be formed as an edge surface 5 of an injector by means of a laser cutting in an oblique direction of one end thereof, if necessary. The tubular body 2 can be configured to transmit applied vibration to the inside of the tube, and may be made of flexible material like rubber or plastic. A diameter of the tubular body 2 can, for example be in a range from hundreds to decades of μm. For uses such as drawing blood piercing human skin or medicine dosing, a range from 500 to 50 μm can be used in order to relieve a psychological burden feeling pain. The fabrication of such a thin tube can be manufactured by drawing, in a case where the tubular body 2 is metallic thin tube. In a case where the thin tube is smaller in diameter, it can be manufactured by, for example, a spattering pile method. For example, it may be referred to Japanese Patent Unexamined Laid-Open Publication No. 2004-232077.

A plurality of vibrating ring bodies 3 are arranged to space a constant interval, and have a piezoelectric element 3a formed like a ring shape and metal electrodes 3b, 3c provided in an inner and outer surface. The vibrating ring body 3 is integrally formed to be in a block and a surface of the inner circumference thereof is in contact with the tubular body 2. The vibrating ring body 3 may be integrally formed by the spattering pile method to be in a block together with the tubular body 2, in a case where the diameter thereof is less than or equal to 500 μm (decades of μm). For example, in a case where the tubular body 2 is beyond 1 mm in diameter and 5 cm in axial length, the vibrating ring body 3 and the tubular body 2 may be separately manufactured to form in a block by adhesives or by thermal procedures. In addition, it is preferable to have an even the number of the vibrating ring bodies 3.

The piezoelectric element 3a can be, for example, PZT (lead zirconate titanate) element, and can be a solid solution of Perovskite type $PbZrO_2$ and $PbTiO_3$ to show a property of ferroelectrics. The piezoelectric element 3a and metal electrodes 3b, 3c are integrally arranged in a block to the tubular body 2, for example, by spattering, depending on the size thereof.

The metal electrodes 3b, 3c are, for example, made of metallic thin film such as platinum, gold, or silver thin film.

The metal electrodes 3b, 3c may be an alloy or the other conductive material to be able to apply the voltage to the piezoelectric element 3a.

In this embodiment, the voltage supply means 4 is used as an energy supply means. The voltage supply means 4 is designed to apply the energy to vibrate the piezoelectric element 3a. The voltage supply means 4 can be provided with two voltage sections 4a, 4b applying the voltage in order to generate different vibrations, depending upon whether the piezoelectric element 3a is placed at an even position or an odd position. The voltage supply means 4 is, for example, constituted such that the piezoelectric element 3a placed at an even position and the piezoelectric element 3a placed at an odd position are mutually different in amplitude of voltage, and a waveform of voltage is different depending upon the frequency. This voltage has, for example, a relationship shown in the following expressions (1) and (2).

Expression 1

$$V_1 = A_{ch1} \sin 2\pi f_{ch1} t \tag{1}$$

Expression 2

$$V_2 = A_{ch2} \sin 2\pi f_{ch2} t \tag{2}$$

Where $A_{ch1}$ and $A_{ch2}$ are amplitudes based on output voltage, $f_{ch1}$ and $f_{ch2}$ are applied frequencies, t is a time, the number of ch1 and ch2 correspond to numbers of applied alternative current, $V_1$ is the voltage of the piezoelectric element placed at an odd number, and $V_2$ is the voltage of the piezoelectric element placed at an even number.

The frequency in expression (1) and (2) is preferable in order to satisfy a condition of the following expression (3).

Expression 3

$$f_{ch2} = n f_{ch1} \text{ or } 1/n f_{ch1} \tag{3}$$

The 'n' in expression (3) is an integer except zero.

As shown in expression (3), the vibration changes according to either an even position or an odd position of the piezoelectric element 3a such that the progressive wave is generated in the tubular body 2. The liquid is transmitted from one side to the other side according to the generated progressive wave. In the relationship between f ch1 and f ch2, it is preferable that one frequency is equal to a multiple of the other frequency, or that one frequency is equal to an inverse number of a multiple of the other frequency.

Though both of the above piezoelectric elements 3a receive data composed of sine curve waves, the data may be shifted in phase to become a relationship between a sine curve wave as one data and a cosine curve wave as the other data, and applied to the piezoelectric element 3a in a different wave cycle.

As shown in FIG. 1, the voltage supply means 4 and the metal electrode 3b are electrically connected through the connecting portion 3d formed on the surface of the tubular body 2 by wire bonding etc. The voltage supply means 4 and the metal electrode 3c are electrically connected directly on the surface of the metal electrode 3c by wire bonding etc.

A portion surrounding the tubular body 2 and the vibrating ring body 3 is covered by a cover 7, which is, for example, a rectangular prism or a cylindrical prism made of plastic material with one end and the other end of the tubular body to be exposed. The voltage supply means 4 and the portion of the tubular body 2 and the vibrating ring body 3 are configured to be connected by an electric code 6a, thus to be kept apart. The voltage supply means 4 is provided in a box-shape power source 6 to actuate as a control section. The box-shape power source 6 is provided with a display 6b, a power source switch 6c, and a control tab 6d, 6d, etc.

An example of a method for manufacturing the functional thin tube device will be described with reference to FIG. 3. FIG. 3A, FIG. 3B, and FIG. 3C are explanatory views showing schematically steps for manufacturing the thin tube (tubular body and vibrating ring body) of the functional thin tube device.

In this example, a portion of the thin tube of the functional thin tube device 1 is formed by a spattering pile method. The spattering pile method is a method for making a film such that rare gas such as Argon introduced in vacuum is ionized, the ionized particles collide with a target, and the particles reflected on the target reach a base plate (a core material). As a concrete example, the covered film made of titanium on a surface of core material W made of copper is formed by the spattering pile method. The tubular body 2 is made to dissolve and eliminate the core material W made of copper at a manufacturing step or a final step by an etching liquid such as an acid. Silver (gold, platinum) thin film is formed as the metal electrode 3b, 3c in the tubular body 2. Then, the thin tube is constituted to form silver (gold, platinum) thin film as the metal electrodes 3b, 3c in the tubular body 2 and to form the PZT element in a ring shape as the piezoelectric element 3a. The manufacturing step of the functional thin tube device 1 will be described in the following.

Figure 3A:
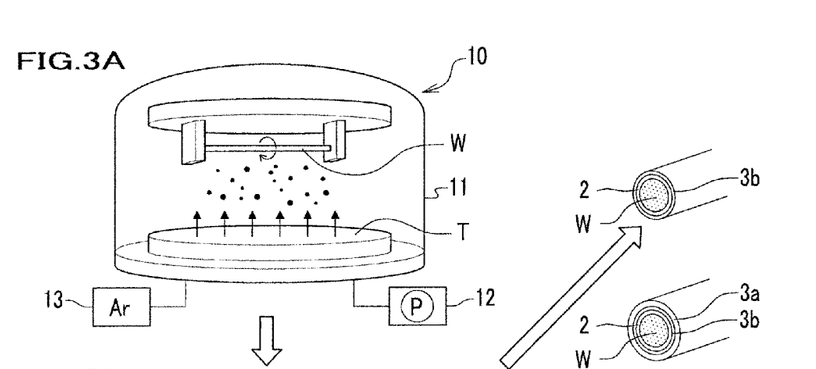
FIGS. 3A to 3C are explanatory views showing steps for manufacturing the thin tube of the functional thin tube device according to embodiments of the present invention.

As shown in FIG. 3A, thin wires made of copper as a core material W in the vacuum receptacle 11 of the spattering device 10 are set, and a target material T made of Titanium is set. Next, the vacuum receptacle 11 is drawn to be in vacuum by a vacuum pump 12 to introduce the rare gas such as Argon in an introducing tube 13. In case of spattering, the core material W is constituted to rotate around an axis of the core material W with the both ends thereof to be grasped. Then, the core material W forms a film of the target material in a state as rotated at 1 to 5 rpm by a motor controlled by a DC motor control. Though a thickness of the film is formed in a range between 5 to 20 μm as one example, it can be appropriately controlled by changing a spattering period.

After a film of the target material T is formed on the core material W, the film formed in the vacuum or in Argon atmosphere (preferably $10^{-5}$ Pa) is thermally processed at a re-crystallized temperature thereof in a vacuum furnace to avoid a hydrogen embrittlement. The thermal procedure enables the film to re-crystallize. In addition, by arranging a heater in the vacuum receptacle 11 (for example, installing in a rectangular portion grasping the core material W) the film material can be thermally processed through the core material W, and also thermally processed in the atmosphere of air with an electric furnace, depending upon the film material. After the thermal procedure, the tubular body is taken out from the vacuum receptacle 11.

Figure 3B:
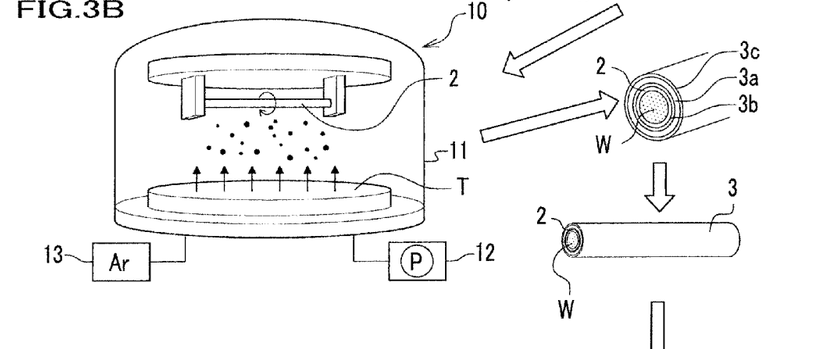
Figure 3C:
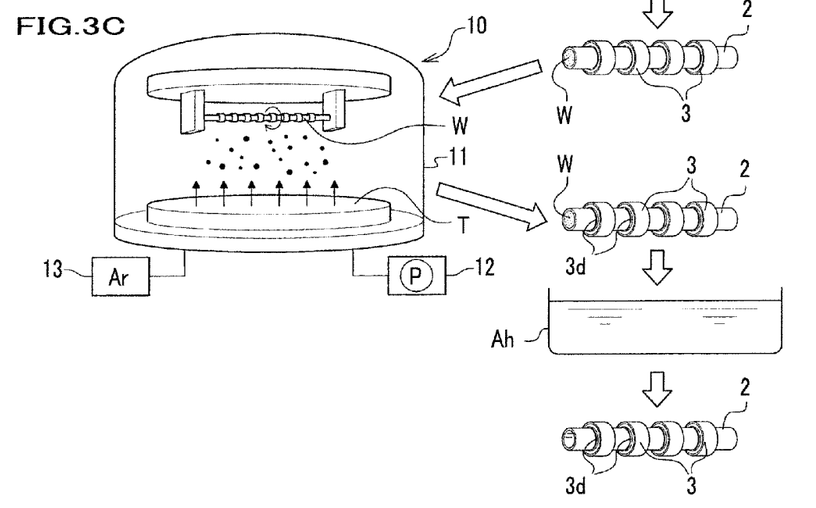

Next, as shown in FIG. 3B and FIG. 3C, the tubular body 2 is set in the vacuum receptacle 11 to set the material for forming an electrode, for example, the target material made of silver (platinum, gold). Then, the target material is formed in the prescribed thickness of film to be taken out through the thermal procedure. Further, the PZT element of piezoelectric element 3a is set as a target material to form the prescribed thickness of film on an electrode's film and to be taken out through the thermal procedure. The silver target material for forming the electrode is, again, set to form a silver film on the piezoelectric element by a repetition of the same procedures as the above. In such a way, the tubular body 2 is rendered to be silver film, piezoelectric element, or a state forming a silver film thereon, and removed by a removing means such as lift-off method or FIB to be ring-shape members having the prescribed width and to keep a constant interval among the ring-shape members. Thus, the ring-shape vibrating ring body 3 can be formed to be a constant interval in an axial direction of the tubular body 2. In case of the lift-off method, masking is required before forming a film of PZT.

When forming the vibrating ring body 3, an inorganic acid such as nitric acid, which is a corrosive medium, etches the core material W to eliminate the core material W from the tubular body 2. In addition, the timing for etching the core material W may be after forming the tubular body 2.

The tubular body 2 and the vibrating ring body 3 form a connecting portion 3d or a connecting circuit for connecting the metal electrode 3b, 3c to the electric power source in the prescribed position of the tubular body 2. In the alternative, an ink-jet printer etc., can be used to form the connecting circuit by laser sintering, and to connect the electric cable (code 6a) from the outside at one end thereof. In addition, the inside metal electrode 3b may form the connecting portion by remaining wider in width than the width of the piezoelectric element 3a.

In the functional thin tube device 1 as manufactured, the tubular body 2 can be, for example, less than or equal to 500 μm in diameter and more than or equal to 5 μm in thickness. In this example, the tubular body 2 is formed to be 50 μm in diameter (outer diameter) and 12.5 μm in thickness. In addition, the length of the tubular body 2 can be formed in a range from several millimeters to several centimeters, depending upon a size of the vacuum receptacle 11. The size of 50 μm in diameter is the approximately same size as the mouth of the female mosquito. In a case where the functional thin tube device 1 is 50 μm in diameter, the injector can pierce human skin without pain to a human body, in order not to form an edge surface of the injector at one end of the tubular body 2.

After the tubular body 2 is formed by the spattering pile method, a method for making a pipe where the core material W etched, is a so-called bottom-up manufacturing method, which dissolves only a substrate material by a corrosive liquid after forming a film on a surface of the wire-shape substrate material as a target material such as thin tube material is rotated. Thus, the extremely thin tube having an appropriate inner and outer diameter, and having an appropriate shape can be manufactured.

Figure 4A:
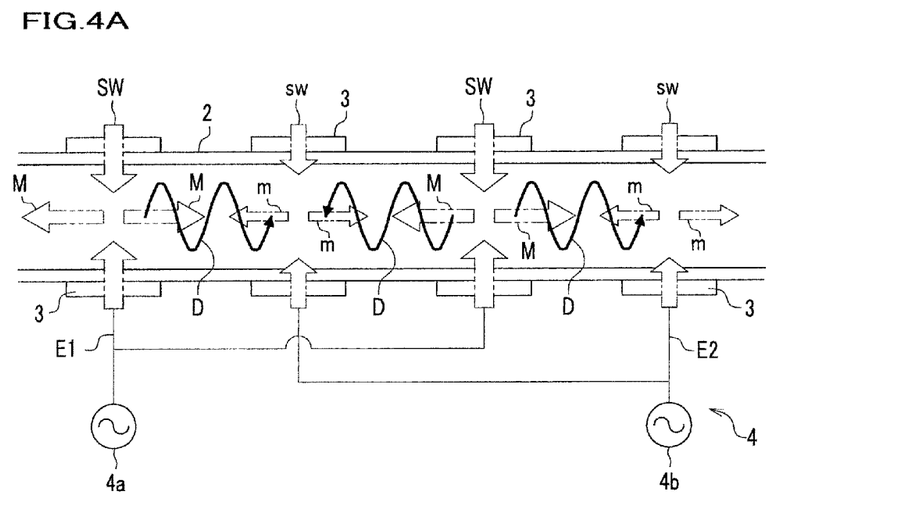
FIG. 4A is a schematic view showing, in cross section, a relationship between vibration and a progressive wave transmitting through a tube when a vibrating ring body of the functional thin tube device relating to the present invention vibrates.
Figure 4B:
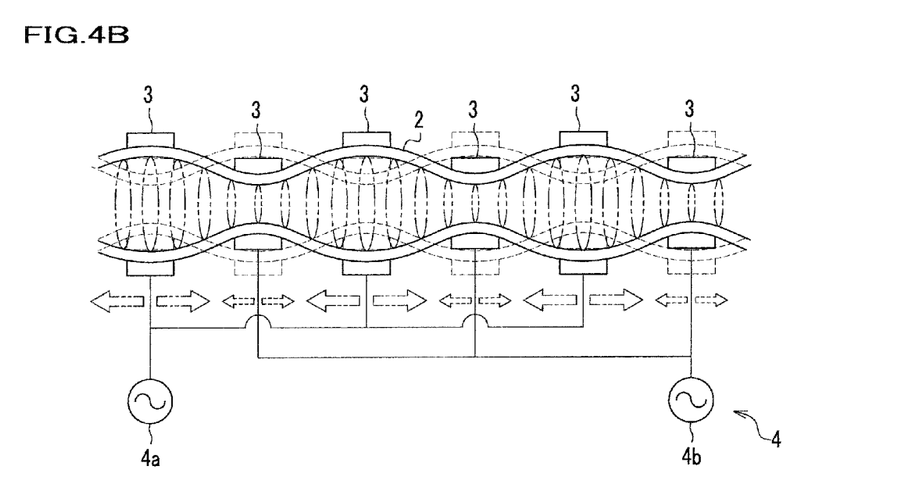
FIG. 4B is a schematic view showing a mechanical movement of the thin tube.
Figure 5A:
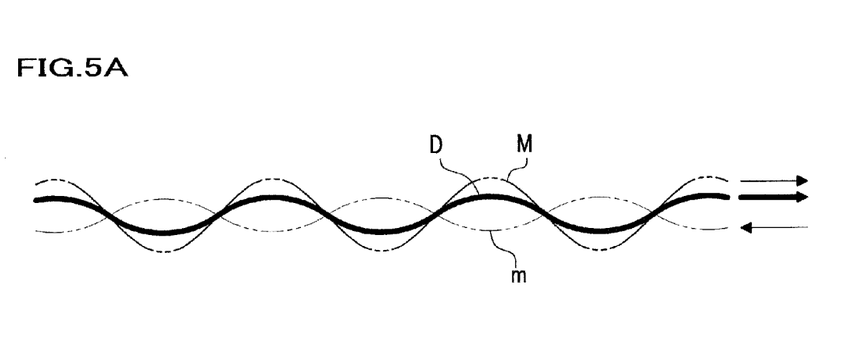
FIGS. 5A to 5C are schematic views showing the progressive wave in a tubular body of the functional thin tube device according to embodiments of the present invention.
Figure 5B:
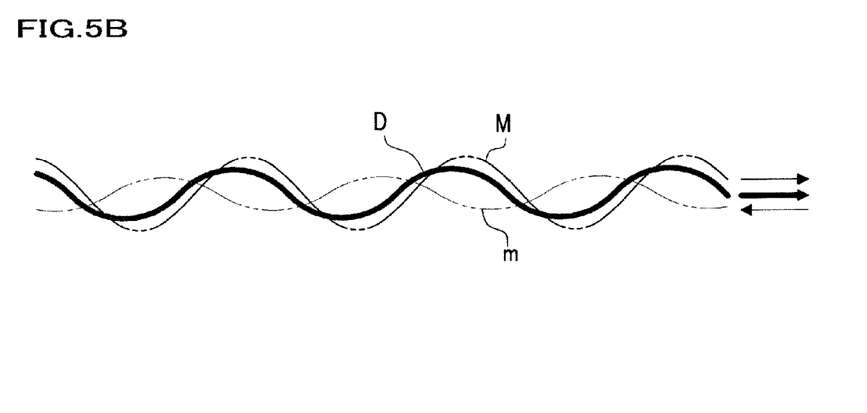
Figure 5C:
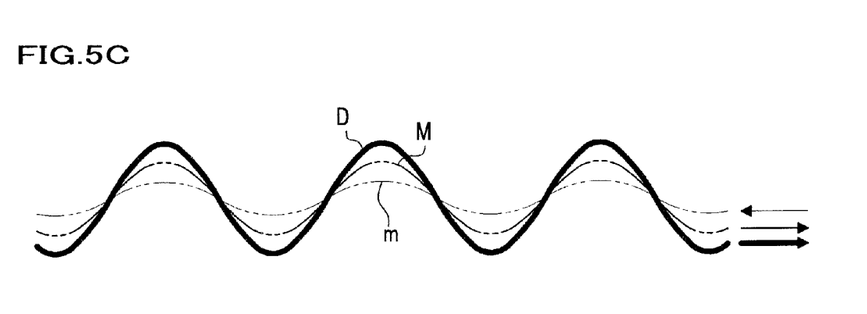
Figure 6:
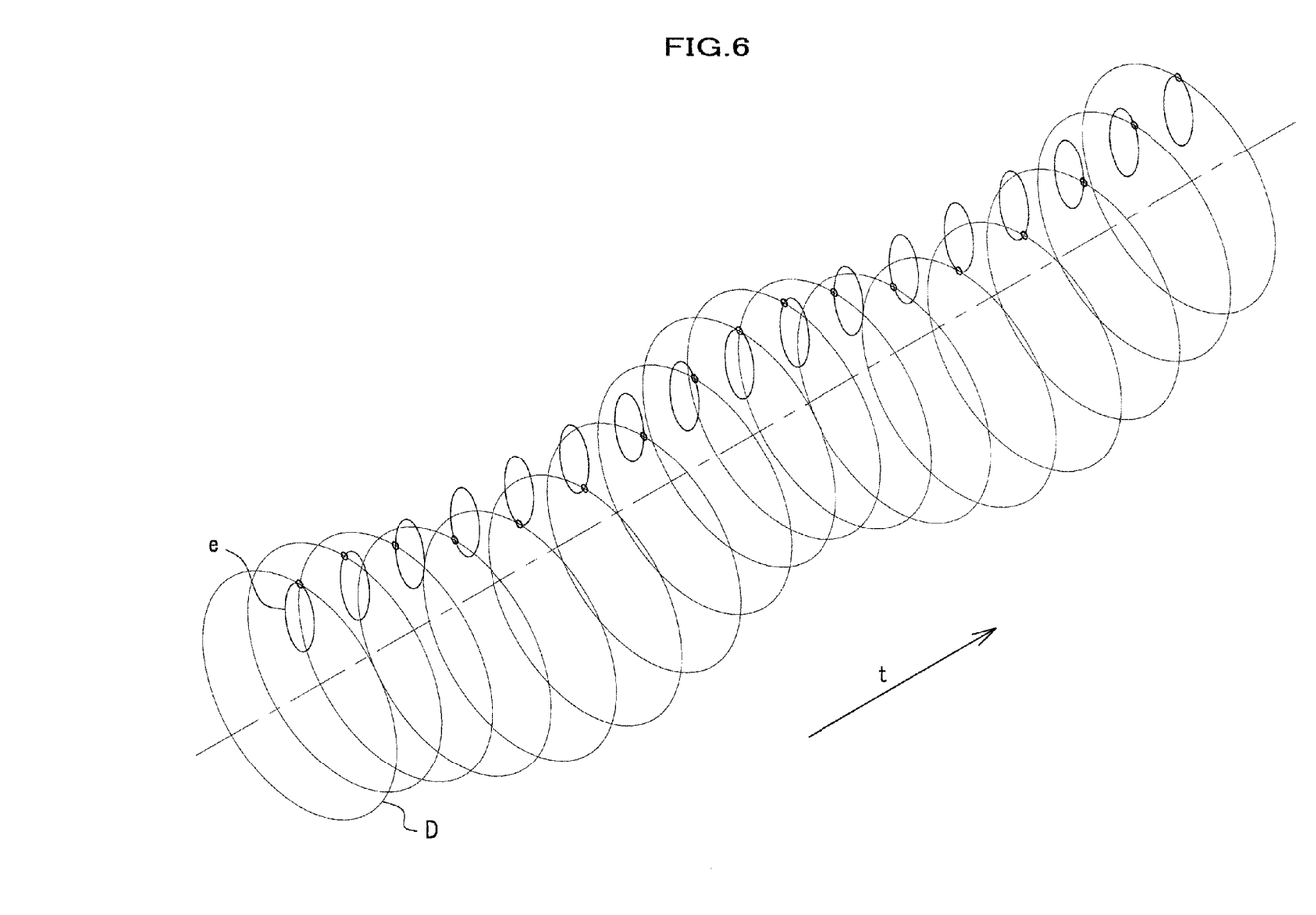
FIG. 6 is a schematic view showing a movement of the progressive wave and an ellipsoidal orbit of the functional thin tube device.
Figure 7A:
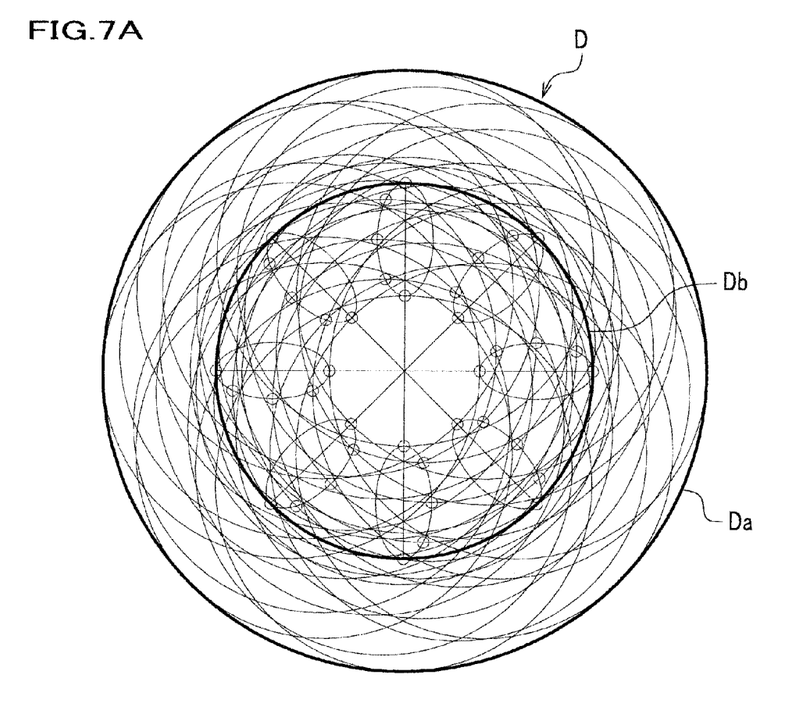
FIG. 7A is a front view showing schematically a relationship between the progressive wave and the ellipsoidal movement in the tubular body of the functional thin tube device.
Figure 7B:
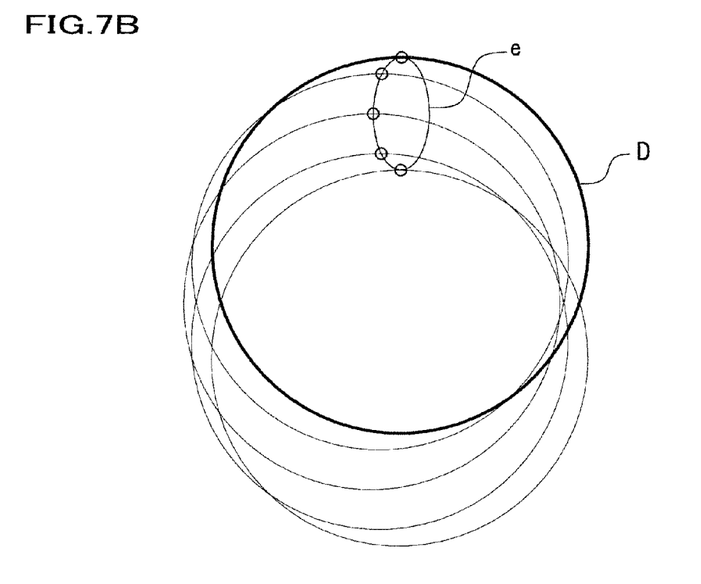
FIG. 7B is a schematic partial front view showing a wave of the progressive wave.

Next, an operation of the functional thin tube device 1, will be described, with reference to FIG. 4 to FIG. 7. FIG. 4A is a schematic view showing in cross section a relationship between the vibration and the progressive wave transmitting through the tubular body in case of vibrating the vibrating ring body of the functional thin tube device. FIG. 4B is a schematic view showing the thin tube replaced by a mechanical actuation. FIG. 5A to FIG. 5C are schematic views showing a state of the progressive wave in the tubular body of the functional thin tube device. FIG. 6 is a schematic perspective view showing a movement of the progressive wave in the tube of the functional thin tube device. FIG. 7A is a schematic front view showing a relationship between the progressive wave and the ellipsoidal movement in the tubular body of the functional thin tube device. FIG. 7B is a partially schematic front view showing the progressive wave.

As shown in FIG. 4A, when the vibrating ring body 3 receives the voltage from the voltage supply means (box-shape power source 6), the vibrating ring body 3, placed at an odd position or at an even position is respectively designed to generate standing waves by breathing vibration SW, sw peculiar to the ring-shape piezoelectric body. A standing wave means a wave which remains on the spot and not vibrated without advancing the waveform. In addition, a polarized direction of the vibrating ring body 3 is formed to propagate from the center of the tubular body 2 in a radial direction.

In the piezoelectric element 3*a*, an alternative voltage having a phase difference such as a sine wave at an odd position and a cosine wave at an even position is applied thereto, and the two alternative voltages different from the frequency is applied. The generation of the progressive wave M and m caused by the alternative voltage E1 and E2 generates a synthetic progressive wave generating a synthetic wave, that is, an ellipsoidal movement resulted from the two progressive waves M, m. Then, as shown in FIG. 4B, the tubular body 2 vibrates with a mechanical movement, that is, peristaltic movement to be approximately the same state transporting the liquid from one side to the other side.

As shown in FIG. 4A, a plurality of the vibrating ring bodies 3 can be arranged at a constant interval on the tubular body 2. In a case where an alternative voltage (for example, expression (1) and (2)) having a different phase and a different frequency is applied to the vibrating body 3 placed respectively at an odd position or an even position, the vibrating velocity of the vibrating ring body 3 changes according to the position. As shown in FIG. 4A, a relationship between the emitted wave M and the reflected wave m is generated in the tubular body 2, considering a direction of the collision between the two progressive waves M, m generated respectively by the breathing vibration SW, sw of the vibrating ring body 3 generated by applying the alternative voltage. The wave for transporting the liquid inside the tube as a synthetic wave of the emitted wave M and the reflected wave m, that is, a synthetic progressive wave D having an ellipsoidal orbit is generated in the liquid as referred to FIG. 5: a real progressive wave D).

As shown in FIG. 4A, the fluid just under the vibrating ring body 3 expands in the left and right direction as progressive waves M, m generate the same progressive wave as transmitted from each vibrating ring body 3 (an image striking the fluid in the tube by PZT element). As shown in FIG. 4A, considering the emitted wave M (a wave directing to the right side in the figure) generated at the vibrating ring body 3 placed at an odd position and the reflected wave M (a wave directing to the left side in the figure) generated at the vibrating ring body 3 placed at an even position, the emitted wave M and the reflected wave m are, in principle, waves for advancing in the opposite direction, as shown in FIG. 5. As a whole, the liquid is transported as the synthetic progressive wave D having an ellipsoidal orbit in the direction of an emitted wave M according to the above synthesis (in this description, as the vibration of PZT placed at an odd position is large, the liquid flows in an advancing direction of the progressing wave as generated by the above.)

In the tubular body 2, the synthetic progressive wave D having the ellipsoidal orbit as synthesized is generated by the vibration of the vibrating ring body 3 to vibrate the liquid in the tubular body 2. The synthetic progressive wave D is a progressive wave having an ellipsoidal orbit e to generate an ellipsoidal movement at an appropriate point of an inner surface of the tubular body 2 as vibrated by the vibrating ring body 3, as shown in FIG. 6. The ellipsoidal movement moves toward an advancing direction to move a point of the circle on the ellipsoidal orbit e, in a case where a point of the circle in depicting a wave of the synthetic progressive wave D as a circle is designated as a standard. Thus, as shown in FIGS. 5A to 5C, the ellipsoidal movement fluctuates in an amplitude of the wave, as seen from the side. Then, the liquid in the tube is transported by the synthetic progressive wave D in a direction of the synthetic progressive wave. As shown in FIG. 7A and FIG. 7B, it is estimated that the movement on the ellipsoidal orbit e generates a large amplitude of wave Da and a small amplitude of wave Db, as seen from the front side of the synthetic progressive wave D.

As a condition for generating the synthetic progressive wave D having an ellipsoidal orbit, a fluctuation of the displacement of the vibrating ring body 3 is controlled by changing the applied voltage and frequency (for example, referred to the above-mentioned expression 1 and 2). In a case where the sympathetic frequency of the tubular body 2 is applied to the vibrating ring body 3 placed at an odd position according to the present invention, the frequency other than the sympathetic frequency is applied to the vibrating ring body 3 placed at an even position. This means that the vibrating ring body 3 placed at an odd position generates a maximal displacement and the vibrating ring body 3 placed at an even position generates a smaller displacement than the maximal displacement. This applies in a case where an inverse frequency is applied to the vibrating ring bodies 3 placed at an odd position or at an even position.

The other condition for generating the synthetic progressive wave D having an ellipsoidal orbit e is a timing control superposing the wave. This is caused by the displacement of two vibrating ring body 3 so that the synthetic progressive wave D (thick line in FIG. 5) as synthesized by collision results in a relationship of the above-mentioned expression 3. This condition is satisfied with that the frequency applied to the vibrating ring body 3 placed at an odd position and an even position has a relationship of a multiple or an inverse number of the multiple.

The disposition of even numbers of the vibrating ring body 3 can make faster a flow of the synthetic progressive wave D. The amount of the applied voltage slants toward a direction for transporting the fluid to cancel a restrictive condition in which a number of the vibrating ring bodies 3 must be an even number. Then, the loss caused by the offset among the synthetic progressive waves D can be decreased. Thus, the improvement of pump performance of the functional thin tube device will be expected.

Preferably, the voltage applied to the piezoelectric element 3*a* decreases from upstream to downstream in the advancing direction. The progressive waves are controlled by a voltage gradient such that one wave does not influence other waves among the progressive waves, so as not to cancel each other. As a result, the high flow speed of the wave can be obtained. In this case, the number of the piezoelectric elements 3*a* is not required to be an even number. Further, instead of the voltage gradient, for example, the resistance arranged between the piezoelectric element 3*a* and the power source can result in a gradient in an amplitude of wave of the progressive wave M in the tubular body 2 because of the decrease of the amplitude of wave to have the same effect as the above.

In addition, the explanation in the tubular body 2 of the above-mentioned functional thin tube device 1 is similar to a principle of an ultrasonic motor in view of a use of the synthetic progressive wave D having an ellipsoidal orbit e. However, although an ultrasonic motor excites the progressive wave in a vibrating body and is used as a frictional actuation with a frictional material, embodiments of the present invention are designed to transport the fluid by generating the synthetic progressive wave D, having the ellipsoidal orbit e, directly in the fluid inside the tube. In addition, the present invention is adopts a principle of emitting the wave on the wall which the reflecting coefficient is less than 1, and to generate the progressive wave depicting an ellipsoidal orbit by the synthetic wave together with the reflected wave as generated in this occasion.

As above described, the functional thin tube device 1 generates the synthetic progressive wave D without using a check valve to become a micro pump for enabling the fluid inside the tubular body to transport.

Figure 8A:
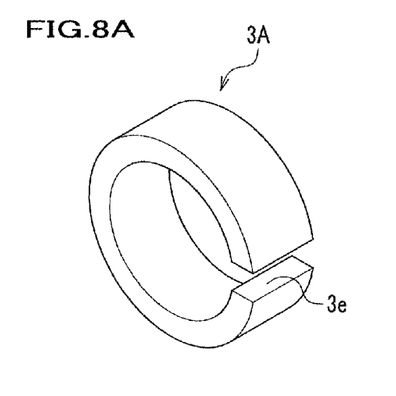
FIG. 8A and FIG. 8B are perspective views showing other embodiments of the vibrating ring body of the functional thin tube device.
Figure 8B:
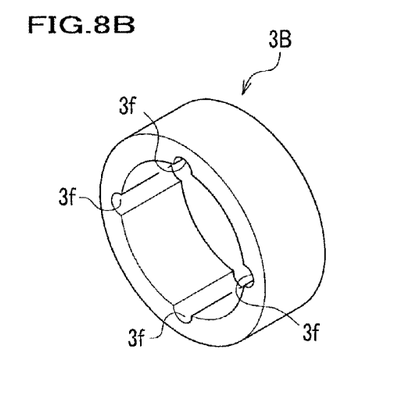

A form of the vibrating ring body 3 may be a for example, as shown in FIG. 8. FIGS. 8A and 8B are perspective views showing another embodiment of the vibrating ring body. As shown in FIG. 8A, a notch portion 3e is provided in the piezoelectric element 3A (PZT element) along an axial direction of the tubular body 2. As shown in FIG. 8B, a concave groove 3f is formed in the side of inner circumference of the piezoelectric element 3B (PZT element) along an axial direction of the tubular body 2. As a result, stresses which might present large displacement can be avoided, enabling formation of a large progressive wave. In a case where the concave groove 3f is formed in the side of outer circumferences of the PZT element, the same effect can be obtained. In any case, it is desirable to avoid these stresses which can prevent large displacement. The fact that the displacement increases by the formation of the notch portion 3e or the concave groove 3f in the piezoelectric element 3A, 3B has been already known and verified by an analysis of the finite element method. In this case, further increase of the displacement can be obtained by the two-layer constitution piling the piezoelectric element 3A (3B) to realize an improved fluidized function of the liquid.

EXAMPLE

Figure 9:
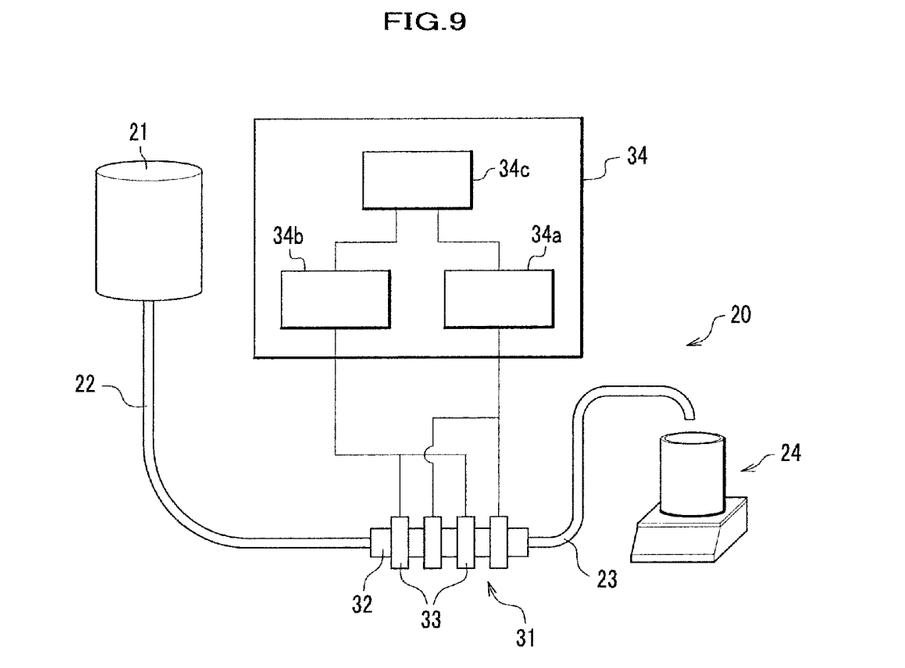
FIG. 9 is a schematic view showing a constitution of an experimental apparatus as used in an example of the functional thin tube device according to embodiments of the present invention.

In the following, an example using a silicon tube, which is large in diameter, will be explained to ascertain the function of the functional thin tube device according to an embodiment the present invention. The present invention is not limited to this example. FIG. 9 is a schematic view showing a constitution of an experimental device 20 of the functional thin tube device 1.

As shown in FIG. 9, a silicon tube 32, which is a tubular body, and four ring-shaped PZT elements 33, which is of being a vibrating ring body mounted on the silicon tube 32, are prepared. The micro pump 31, which is a thin tube, is constituted to mount the PZT elements 33 on the silicon tube 32 with the PZT elements spaced at a 10 mm interval. In the ring-shaped PZT element and the silicon tube 32 as mounted in the micro pump 31, the size of the PZT element is 12.5 mm in diameter, 13.5 mm in diameter, and 5 mm in width, respectively. d is an inner diameter, D is an outer diameter, and H is a width, respectively, and a folded-back electrode is applied not to prevent displacement in the inner direction. The silicon tube 32 is flexible and it has 10 mm in inner diameter and 12 mm in outer diameter in harmony with an inner diameter of the ring-shape PZT element 33.

In addition, the ring-shaped PZT element 33 and a silicon tube 32 are adhered, for example, by a CEMEDINE (Registered Trademark), which is a commercially available adhesive. The silver electrode (not shown) is applied on an outer surface and an inner surface of the ring-shape PZT element 33. The ring-shaped PZT element 33 is driven and vibrated by applying the alternative voltage from the voltage supply means 34. This vibration causes the progressive wave to generate in the fluid inside the silicon tube and generates an ellipsoidal movement at an appropriate point of the fluid. Then, the fluid inside the tube is transported in accordance with the deviation from the initial point because of the viscosity of the fluid. A situation generating the progressive wave can be changed by the influence of an element of the voltage and the frequency applied to the ring-shaped PZT element 33. Then, a condition for enabling the velocity of the fluid inside the tube to control is carefully considered. An applied waveform is taken as a sine wave and a cosine wave in the direction of polarization directing to the diametrical direction from a center of the silicon tube.

The displacement of the ring-shape PZT element effects the transportation of the fluid inside the tube. The product C-9, made by FUJI Ceramics Co. Ltd. is used as the ring-shaped PZT element in this example. The piezoelectric constant d33 of PZT as used in this example is 718 μm/V. As the displacement of ring-shaped PZT element 33 is extremely small, the displacement in a state attaching the silicon tube 32 is measured by a laser doppler vibrator. A voltage of 60 Vp-p is applied to the ring-shaped PZT element to change the frequency. The effect, as above obtained, is shown in FIG. 11A and FIG. 11B.

Figure 11A:
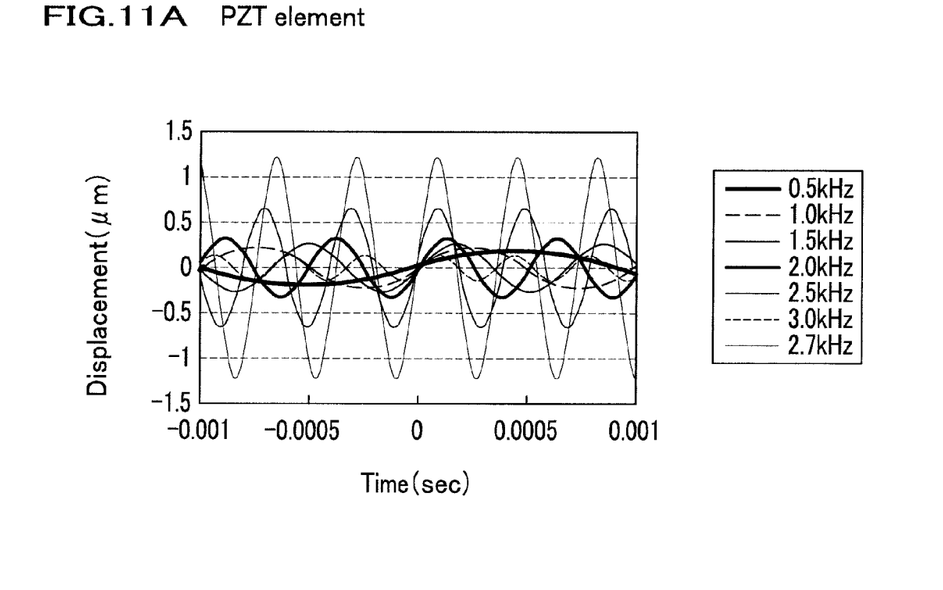
FIG. 11A and FIG. 11B are graphs showing a change of amplitude of wave relative to a lapsed time in an example of the functional thin tube device of the present invention.
Figure 11B:
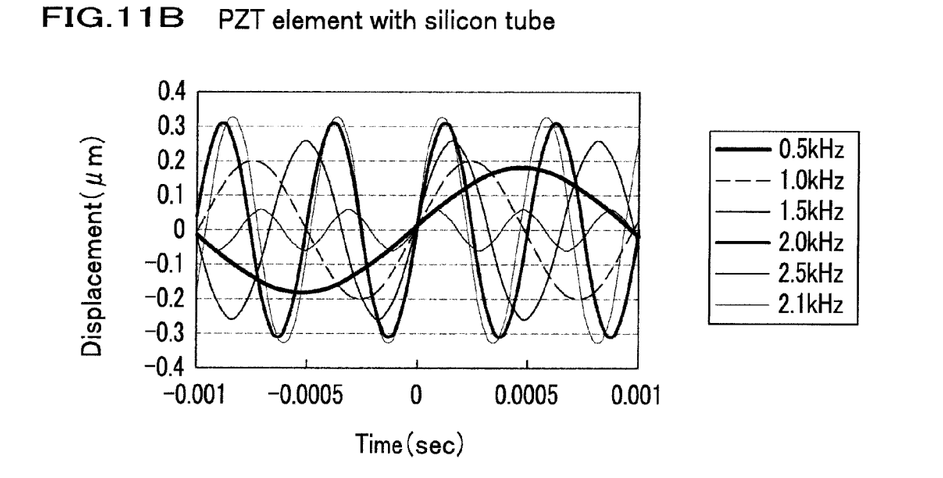

FIG. 11A is a graph showing a relationship between the displacement and time of the ring-shaped PZT element 33. FIG. 11B is a graph showing a relationship between the displacement and time when the ring-shaped PZT element 33 is integrally mounted to the silicon tube 32. As shown in FIG. 11B, the ring-shaped PZT element 33 has a maximal displacement 0.33 μm at sympathetic frequency 2.1 kHz, thus to ascertain the vibration. Although the displacement of the ring-shape PZT element is concerned with the characteristics of fluidized function of the micro pump 31, the problem of the ring-shaped PZT element 33 is, in general, overcome by a bimorph type piling two sheets or a multi-layer type pasting and piling a plurality of sheets.

In the liquid transportation by vibration in tubular body, the more amounts of vibration and displacement, the more amounts of the liquid transportation. Although it has been known to be a large amount of vibration or displacement in a plate-like bimorph type or a multi-layer type, a preferable form is unknown in case of a ring shape. The mono-morph type ring-shaped PZT element 33 is used as the micro pump 31 in this example. This is based on the two-layer type being designed to pile the PZT element, which is the same direction as the polarized direction and a size larger, is estimated to be insufficient as the multi-layer type.

As shown in FIG. 9, in an experimental apparatus 20 for estimating the volume of flowing of the liquid inside the tube, a micro pump 31 is mounted parallel to the base plate (not shown). In a state that the voltage and the frequency are applied from the reservoir tank 21 through the tube 22 connecting to one end of the micro pump 31 to the ring-shaped PZT element 31, the flow rate of the liquid flowing by a difference in height (i.e. a pressure difference) between a water level in the reservoir tank 21 and a height of the other end of the tube 23 through the tube 23 connecting to the other of the micro pump 31 has been measured. The flow rate is calculated to get the mean value by measuring the volume of flow and the time as flowed by the measuring device 24 connected to the tube 23, considering that the water level in the reservoir tank 21 changes together with a lapse of time. The initial flow rate resulted in 5.04 ml/sec. Next, in a case where the different waveform in voltage and frequency is applied to the ring-shaped PZT element 33, the flow rate is sought and estimated by comparing with the initial flow rate.

Figure 10A:
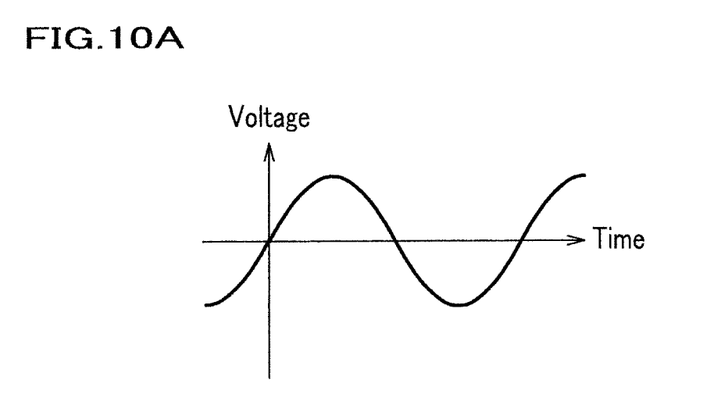
FIGS. 10A to 10C are graphs showing a waveform of applied voltage in an example of the present invention.
Figure 10B:
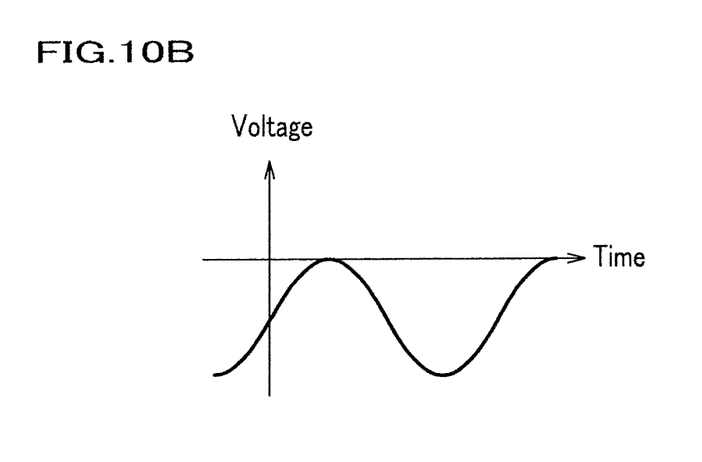
Figure 10C:
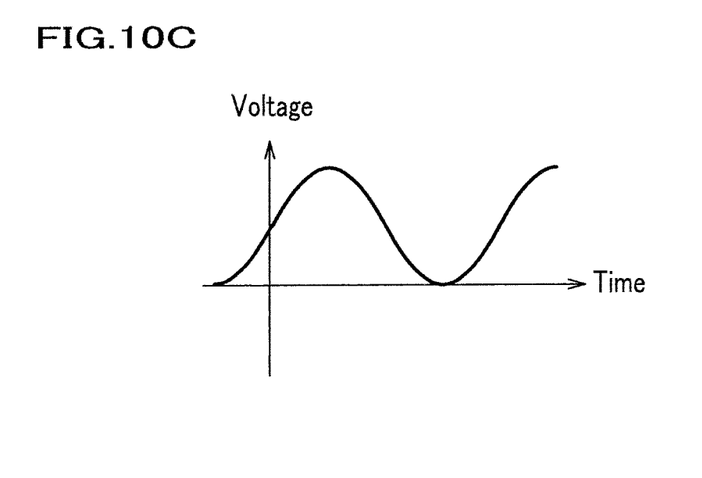

In this flow functional experiment, the positive voltage is applied to the PZT element as shown in FIG. 10B. As shown in FIG. 10A, although normal alternatively voltage is a waveform changing alternatively in a plus side or in a minus side as taken a horizontal axis at zero as a standard line, it is able to limit the displacement of the ring-shaped PZT element 33 to be one direction by the offset in the negative voltage (piling an apex in the plus side of the waveform on a horizontal axis). As the polarized direction is a diametrical direction toward the outside in this example, it becomes a compressive vibration in the diametrical direction. Then, as the PZT element does not move to the outside of the diametrical direction and the fluid inside the tube becomes compressed, it is considered to improve a transportation efficiency of the micro pump by an increase of the frictional force. For the other comparison, the negative voltage is applied to the PZT element.

Figure 12:
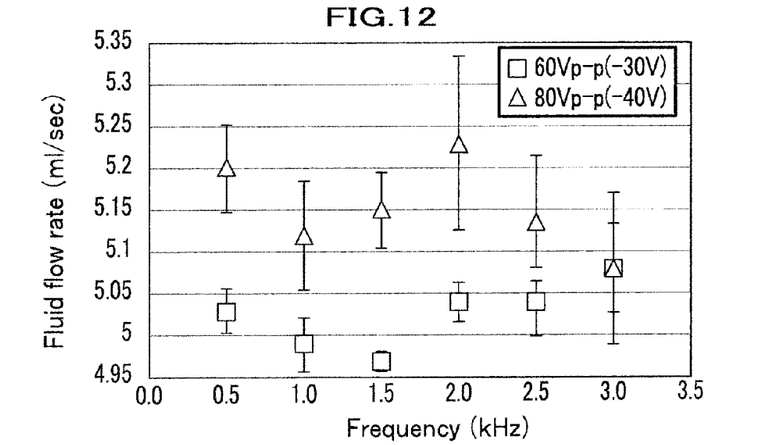
FIG. 12 is a graph of an output frequency from ch2 plotted as a horizontal axis and a flow rate plotted as a vertical axis in an example of the functional thin tube device according to embodiments of the present invention.

In a use of the experimental device 20 as shown in FIG. 9, the sympathetic frequency decreases to 0.8 kHz, when the fluid flows in the micro pump 31. The micro pump 31 is configured to completely mount the silicon tube 32 and the ring-shaped PZT element 33 in this example. In the voltage supply means 34, the frequency emitting from ch1 (34a) is fixed to be 0.8 kHz and the frequency emitting from ch2 (34b) is changed. This corresponds to a change of vibrating interval of the ring-shaped PZT element, that is, corresponds to a phase change of the progressive wave occurring in the fluid inside the tube, Further, two patterns of 60 Vp-p (offset voltage: −30V) and 80 Vp-p (offset voltage: −40V) are applied. The result of a fluidized functional experiment by the above method is shown in FIG. 12. In FIG. 12, an output frequency from ch2 is plotted along a horizontal axis and the flow rate is plotted along a vertical axis. As shown in FIG. 12, an increase of the applied voltage is ascertained to increase the flow rate. The change of the flow rate is considered to be concerned with an increase of the displacement of the ring-shaped PZT element 33 by increasing the applied voltage. Comparing with the initial flow rate 5.04 ml/sec, the applied voltage is ascertained to be able to decrease or increase the flow rate. In addition, the maximal or minimal flow rate remains to be a fluctuation of 3.8 percentage or 1.4 percentage relative to the initial flow rate, respectively.

When the frequency outputting from the ch2 is more than or equal to 3.0 kHz in this example, there was no difference in the change of flow rate in case of the applied voltage 60 Vp-p and the applied voltage 80 Vp-p. Though it is considered to be a decline of the displacement caused by shifting from the sympathetic frequency of the ring-shaped PZT element 33, the fact that it is not able to follow the fluid inside the tube may be considered as the other cause. Though water is applied as an estimating fluid in this example, an application for medical field will be expected. That is, considering the blood having high viscosity, an increase of the friction force in the inner surface of the silicon tube and a followability in the range of the fluid having high-frequency band can be expected, as the blood has a higher degree of viscosity than water.

Figure 13:
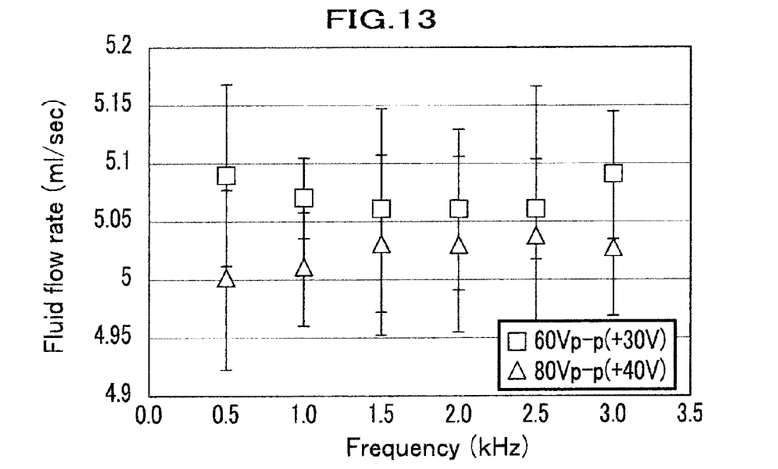
FIG. 13 is a graph of an output frequency from ch2 plotted as a horizontal axis and a flow rate plotted as a vertical axis relating to changing a condition of wave of applied voltage in an example of the functional thin tube device according to embodiments of the present invention.

As a comparison, a change of the flow rate is also verified, in a case where the offset waveform and normal wave are applied to a plus side. At first, the experimental effect is shown in FIG. 13, in a case where the offset alternative voltage is applied to a plus side. The output frequency from ch2 is plotted along a horizontal axis, and the flow rate is plotted along a vertical axis, as well as the case of the offset applied to a minus side. As shown in FIG. 13, though the decrease of flow rate of 0.79 percent is ascertained by increasing the applied voltage, an efficiency of the decrease of flow rate is considered to be not good.

However, the principal point, which is different from the case as an offset waveform as applied to a minus side, enables the decrease of flow rate to be realized by increasing the applied voltage. In this case, the ring-shaped PZT element is limited to the displacement extending the ring-shaped PZT element in a diametrical direction. Thus, as it is considered that a frictional actuation between an inner wall of the silicon tube 32 and the fluid has not occurred, a decrease of the efficiency may be caused by this reason. In this case, it is considered not to be influenced by the frictional actuation on a surface of the silicon tube 32, but by the occurrence of negative pressure in the small displacement of the ring-shaped PZT element. The search in an appropriate condition is considered to improve or increase an efficiency of the decrease of the flow rate owing to the applied voltage. Then, it has proved that the offset waveform applied to a plus side is effective in the decrease of the flow rate inside the tube.

Figure 14:
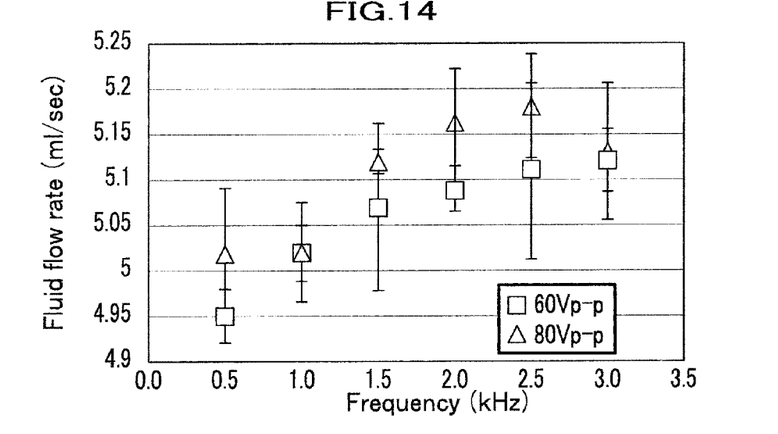
FIG. 14 is a graph of an output frequency from ch2 plotted as a horizontal axis and a flow rate plotted as a vertical axis relating to changing a condition of waveform of applied voltage in an example of the functional thin tube device relating to the present invention.

Next, FIG. 1 shows an experimental effect, in a case where a normal waveform of alternative current is applied without the offset. As well as the case of the offset in a minus side and plus side, the output frequency from ch2 is plotted along a horizontal axis, and the flow rate is plotted along a vertical axis. As shown in FIG. 14, the rate of increase and decrease of the flow rate are shown 2.8 percentages and 1.8 percentages in maximum, respectively. Further, it can be understood that the increase of the flow rate caused by the increase of applied voltage is ascertained, and the flow rate increases with an increase of the output frequency from ch2. However, as well as the case of the offset in a minus side, the difference in the change of flow rate becomes zero in case of the applied voltage 60 Vp-p and the applied voltage 80 Vp-p, when the output frequency from ch2 becomes at least 3.0 kHz. This is considered to be caused by the same reason as the case of an application of an offset waveform in a minus side.

In this example, the decrease of flow rate can be ascertained at a comparatively low situation of the output frequency from ch2, as well as the case of the offset in a minus side. Thus, it has resulted in that the increase rate of the flow rate is inferior to the offset waveform in a minus side, but the decrease rate of the flow rate is superior thereto.

As above mentioned, the functional thin tube device can be smaller and more microscopic in size, as the pipeline composed of tubular bodies and the pump section composing of the vibrating ring body are integrated. Thus, the functional thin tube device can be available for a wide range of uses, for example from a field of MEMS to a medical field such as medicine dosing and drawing blood.

Except the fluidized function, an extremely thin tube itself can behave like a movement similar to a peristaltic movement of an earthworm. If an extremely thin tube having a multi-functional property can be manufactured, the application to a medical field such as an artificial blood vessel can be expected. On manufacturing the thin tube for use in the technique for manufacturing an extremely thin tube, it can be used as a pipeline of the liquid such as blood and liquid chemical. The development of a device, which is operable in an extremely microscopic field such as an area inside human body including blood vessels as being normally inoperable for a man, can be expected.

Though the voltage supply means as one example of an energy supply means and the piezoelectric element as a vibrating ring body have been explained in this description, the means for transforming the energy to a mechanical vibrating energy may be used, for example, titanium dioxide vibrating by means of a supply of photo energy from the energy supply means, or shape memory alloy vibrating by means of a supply of thermal energy from the energy supply means may be used.

As the functional thin tube device is configured to integrate the vibrating ring body having a pump section and the piping forming a portion of the liquid transportation, it is easy to be small in size. Then, it can be used in a small portion (section).

As the functional thin tube device is designed to control the volume of flow or the flow rate of the liquid as transported by displacement, vibrations and a timing control of the vibration of the vibrating ring body, a high quality of micro pumps can be developed.

The functional thin tube device is formed, for example, by a metal to be an edge surface of the injector needle by machining one end thereof, thus to integrate a portion of an injector needle, a pump section, and a tubular body in a block. Then, as the device becomes compact, it is able to have a lower level of invasiveness during injection in the skin of humans and animals, and to relieve the discomfort and burden of patients accompanying with a movement for piercing with an injector.

The functional thin tube device can be extended to a wide range of use thereof by manufacturing the tubular body made of flexible material such as silicon rubber.

The functional thin tube device can make vibration relative to the tubular body to be larger by forming a groove portion and a notch portion in the vibrating ring body. Accordingly, a wide dynamic range to control the flow rate can be obtained in transporting the liquid in the tube body.

The functional thin tube device can make the vibration of the progressive wave for transporting the liquid inside the tube to be larger by corresponding the vibration of the vibrating ring body to the sympathetic frequency of the tube body.

What is claimed is:

1. A functional thin tube device for transporting liquid inside a tubular body from one side to the other side of the tubular body, said device comprising:
a hollow tubular body;
a plurality of vibrating ring bodies mounted in contact with the tubular body spaced an interval along an axial direction on an outer circumference of the tubular body; and
an energy supply means for supplying energy for the vibrating ring bodies,
wherein the energy supply means is configured to generate a first standing wave having a large amplitude of wave at a first set of alternating positions of the vibrating ring bodies, to generate a second standing wave having a smaller amplitude of wave than a displacement of the large amplitude of wave at a second set of alternating positions of the vibrating ring bodies, and to supply the energy to the vibrating ring bodies in order to become a synthetic progressive wave having an ellipsoidal orbit by a pile of the first standing wave and the second standing wave.

2. A functional thin tube device according to claim 1, wherein the energy supply means comprises a voltage supply means, and
the first standing wave and the second standing wave are respectively applied by the voltage supply means as a voltage waveform with different frequency to one side placed at an odd number's position or another side placed at an even number's position of the vibrating ring bodies.

3. A functional thin tube device according to claim 1, wherein the energy supply means comprises the voltage supply means, when an amplitude of wave caused by an output voltage is $A_{ch1}$ and $A_{ch2}$, an applied frequency is $f_{ch1}$ and $f_{ch2}$, time is t, a number in ch1 and ch2 is a number corresponding to a number of the applied alternating current, the frequency is $f_1$ and $f_2$, the voltage of one of the vibrating ring bodies is V1, and the voltage of the other of the vibrating ring bodies is V2,
a first supply voltage for generating one of the first standing wave and the second standing wave is an expression (1), that is, $V1 = A_{ch1} \sin 2\pi f_{ch1} t$, and a second supply voltage for generating the other of the first standing wave and the second standing wave is an expression (2), that is, $V2 = A_{ch2} \sin 2\pi f_{ch2} t$, and when the frequency in the expressions (1) and (2) is an integer n except for zero, an expression (3) is shown by a relationship between $f_{ch2} = n f_{ch1}$ or $(1/n) f_{ch1}$.

4. A functional thin tube device according to claim 1,
wherein the vibrating ring bodies comprise
a piezoelectric element formed in a ring shape, and
a metal electrode provided on surfaces of an inner circumference and an outer circumference of the piezoelectric element,
wherein the energy supply means comprises voltage supply means for applying the voltage to the piezoelectric element.

5. A functional thin tube device according to claim 1,
wherein the vibrating ring bodies have a groove portion or a notch portion, which is formed along an axial direction of the tubular body.

6. A functional thin tube device according to claim 2,
wherein the energy supply means is applied to have a gradient of voltage in order to lower the applied voltage toward a transporting direction of the liquid transporting inside the tubular body.

7. A functional thin tube device comprising:
a hollow tubular body;
a plurality of vibrating ring bodies mounted in contact with the tubular body and spaced an interval along an axial direction in an outer circumference of the tubular body; and
an energy supply means for supplying energy for vibrating the vibrating ring bodies,
wherein the energy supply means is configured to supply energy to be mutually different among the displacement of vibration of the vibrating ring bodies, such that the vibration placed at an even number position or an odd number position of the vibrating ring bodies becomes a sympathetic frequency of the tubular body.

* * * * *